United States Patent [19]

Meijer et al.

[11] 4,193,925
[45] Mar. 18, 1980

[54] PROCESS FOR PREPARING 2-PYRROLIDONE

[75] Inventors: Peter J. N. Meijer; Johannes G. M. Nieuwkamp, both of Geleen, Netherlands

[73] Assignee: Stamicarbon, B.V., Geleen, Netherlands

[21] Appl. No.: 4,474

[22] Filed: Jan. 18, 1979

[30] Foreign Application Priority Data

Jan. 19, 1978 [NL] Netherlands .................. 7800644

[51] Int. Cl.$^2$ .......................................... C07D 207/38
[52] U.S. Cl. .......................................... 260/326.5 FN
[58] Field of Search ............................. 260/326.5 FN

[56] References Cited

U.S. PATENT DOCUMENTS

4,123,438  10/1978  Geurts et al. ............. 260/326.5 FN

*Primary Examiner*—Jose Tovar
*Attorney, Agent, or Firm*—Cushman, Darby & Cushman

[57] ABSTRACT

An improved process for the preparation of 2-pyrrolidone by the liquid phase hydrogenation of succinonitrile in the presence of a hydrogenation catalyst and ammonia, whereafter the resulting hydrogenation product is hydrolyzed with water. A hydrogenation catalyst in the form of a fixed bed is used, and a liquid phase of succinonitrile and liquid ammonia is passed over the catalyst at a temperature of between 50° and 130° C.

5 Claims, No Drawings

PROCESS FOR PREPARING 2-PYRROLIDONE

BACKGROUND OF THE INVENTION

The invention relates to a process for preparing 2-pyrrolidone by liquid phase hydrogenation of succinonitrile by means of a catalyst in the presence of hydrogen and ammonia, and treating the resulting hydrogenated product with water.

A process of this type is described in British Pat. No. 1,494,454, wherein the hydrogenation is carried out with the required catalyst suspended in a liquid phase consisting of succinonitrile in an inert solvent such as pyridine, and under a hydrogen partial pressure of between 1 and 50 atms. However, one of the difficulties encountered in such a process, particularly in large scale continuous production, is that the suspended catalyst must be removed by filtration. It is therefore an object of the present invention to provide an improved process, particularly applicable to large scale continuous production, whereby this difficulty is overcome.

DETAILED DESCRIPTION OF THE INVENTION

It has now been found that the necessity for filtration and separation of the hydrogenation product can be avoided, while still obtaining acceptable yields, by using a catalyst in the form of a fixed bed, and passing the succinonitrile in a liquid phase together with liquid ammonia over the catalyst at a temperature of between about 50° and 130° C. Thus, no filtration is required after the hydrogenation to remove the catalyst, and the process is consequentially very suitable for continuous operation.

The ratio of succinonitrile to ammonia in the liquid phase can be varied within a wide range, but preferably will be between about 5 and 250 g of succinonitrile per 100 g of ammonia.

The partial hydrogen pressure may also be varied within a wide range of between about 100 and 35,000 kPa. However, a partial hydrogen pressure of between about 5,000 and 20,000 kPa is preferred.

The hydrogenation of this invention can be carried out utilizing any known hydrogenation catalyst, such as nickel, cobalt and palladium, and such catalysts can be supported, if desired on a suitable carrier material such as carbon, aluminium oxide or silicon dioxide. By preference a nickel-containing catalyst is used.

The hydrogenation of succinonitrile according to the present invention can be suitably carried out in what is known as a trickle-phase reactor wherein the liquid phase of succinonitrile in liquid ammonia is caused to flow through the fixed catalyst bed, while the hydrogen or the gas containing the hydrogen is passed through the catalyst bed as a counter-current or co-current flow. The liquid phase load on the catalyst may be varied within the range of, for example, between 0.1 and 25 liters of liquid phase per hour per liter of catalyst.

After the hydrogenation of the succininotrile has been carried out, the ammonia may be either fully or partially removed from the resulting reaction mixture and the subsequent treatment of the hydrogenated product with water may be carried out either in the presence or in the absence of ammonia. The treatment of the hydrogenation product with water is carried out in accordance with the known process and the temperature may be varied between about 150° and 300° C. The amount of water likewise may be varied as in the known process between the stoichiometric amount of water required to effect the final reaction to 2-pyrrolidone up to an amount of 20 moles of water per mole of succinonitrile.

The process of the invention will be further illustrated by the following example of a preferred embodiment.

EXAMPLE 0.1 kg per hour of succinonitrile was dissolved in 1.25 kg per hour of liquid ammonia at an elevated presure in a mixer heated at a temperature of 80° C., and the resulting liquid phase was fed via a pump into the top of a vertically arranged metal tubular reactor. The reactor had an internal diameter of 2.1 cm and was one meter in length.

The bottom portion of the reactor contained 275 milliliters of catalyst, and the upper portion of the catalyst contained a layer of 75 milliliters of inert packing material, specifically protruded metal packing of 0.16×0.16 cm size. The catalyst used in the lower portion of the reactor was a commercially available activated nickel catalyst having 50% by weight nickel on an $Al_2O_3$ support. The catalyst was in the form of cylinders having a height of 4.2 mm and a diameter of 4.0 mm. The bulk density of the catalyst was 970 g per liter.

Hydrogen was fed into the top of the tubular reactor, along with the ammoniacal liquid phase, by means of a compressor at a rate of 1,400 liters (0° C. and 100 kPa) per hour. The partial hydrogen pressure within the reactor was maintained at 8,800 kPa. The temperature of the reactor was maintained at 95° C. by means of a heating jacket.

The resulting reaction mixture was discharged from the bottom of the reactor, cooled to 40° C. and separated under pressure into a liquid phase and a gas phase in a separator. Subsequently the ammonia was removed from the liquid phase reaction mixture in an expansion vessel operated at atmospheric pressure. After operation of the reactor for a period of 14 hours, the reaction mixture was collected over the subsequent two-hour period. A 2-gram sample of the resulting product (consisting of 211 g) was analyzed by means of a gas-chromatograph, which showed that no starting product was any longer present in the reaction mixture. The remaining reaction mixture was mixed with 150 g of water and heated at a temperature of 210° C. with stirring in a one liter autoclave for a period of 1.5 hours. After cooling the hydrolized product was analyzed on the gas-chromatograph. It was thus determined that 160 g of 2-pyrrolidone had formed, which corresponds to a yield of 75% calculated with respect to the amount of succinonitrile starting material.

What is claimed is:

1. An improved process for the preparation of 2-pyrrolidone by the liquid phase hydrogenation of succinonitrile by means of a catalyst in the presence of hydrogen and ammonia, the improvement wherein said catalyst is in the form of a fixed bed, and a liquid phase of succinonitrile and liquid ammonia is passed over said catalyst at a temperature within the range of between about 50° and 130° C.

2. The process of claim 1 wherein said mixture contains 5 to 250 g of succinonitrile per 100 g of liquid ammonia.

3. The process of claim 1 wherein the partial hydrogen pressure is within the range of between about 5,000 and 20,000 kPa.

4. The process of claim 1 wherein a nickel-containing catalyst is used.

5. The process of claim 1 wherein said liquid phase is passed over said catalyst at a rate of between 0.1 and 25 liters of liquid phase per hour per liter of catalyst.

* * * * *